United States Patent [19]

Clements

[11] 4,390,015

[45] Jun. 28, 1983

[54] THIGH SUPPORT BRACE

[76] Inventor: C. Dale Clements, 9662 Gurdon, Boise, Id. 83702

[21] Appl. No.: 223,254

[22] Filed: Jan. 8, 1981

[51] Int. Cl.³ .......................... A61F 3/00; A61F 13/00
[52] U.S. Cl. .................................. 128/80 R; 128/133; 269/328
[58] Field of Search ................ 128/80 R, 80 F, 87 R, 128/88, 133–134; 269/328

[56] References Cited

U.S. PATENT DOCUMENTS

| | | | |
|---|---|---|---|
| 2,978,713 | 4/1961 | Scalzitti | 269/328 |
| 3,759,252 | 9/1973 | Berman | 269/328 |
| 3,995,846 | 12/1976 | Frick | 269/328 |
| 4,000,736 | 1/1977 | Bruscemi | 128/80 R |
| 4,181,297 | 1/1980 | Nichols | 269/328 |
| 4,275,472 | 6/1981 | Erck | 269/328 |

Primary Examiner—Michael H. Thaler
Assistant Examiner—C. W. Shedd
Attorney, Agent, or Firm—H. Gordon Shields

[57] ABSTRACT

A support brace for elevating the knees and holding the legs apart includes a curved base support plate secured to a pair of thigh rests having straps for securing the apparatus to a user's thighs.

4 Claims, 7 Drawing Figures

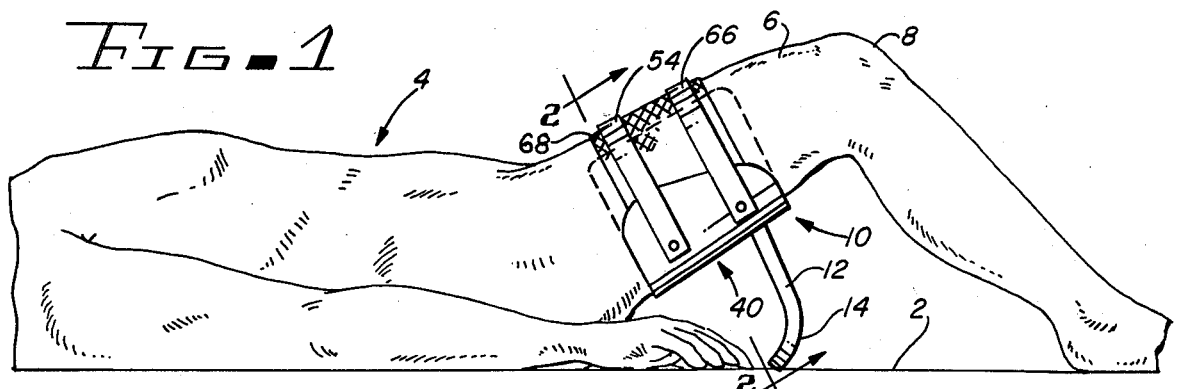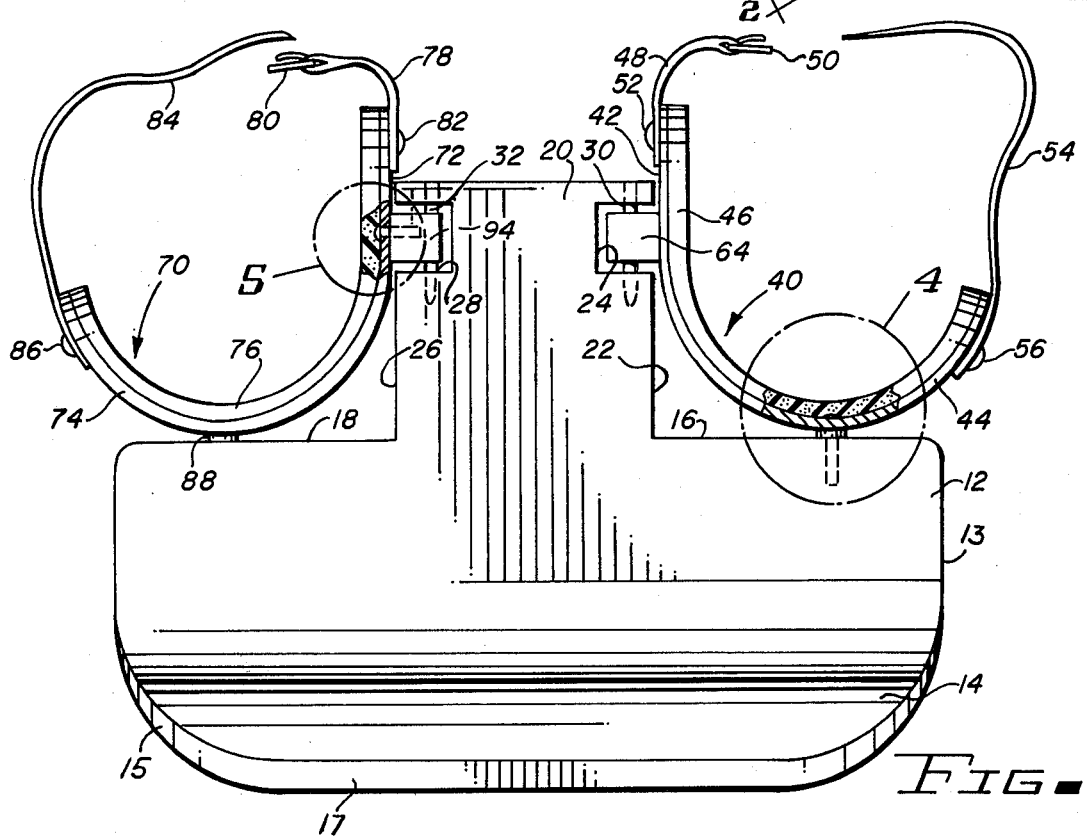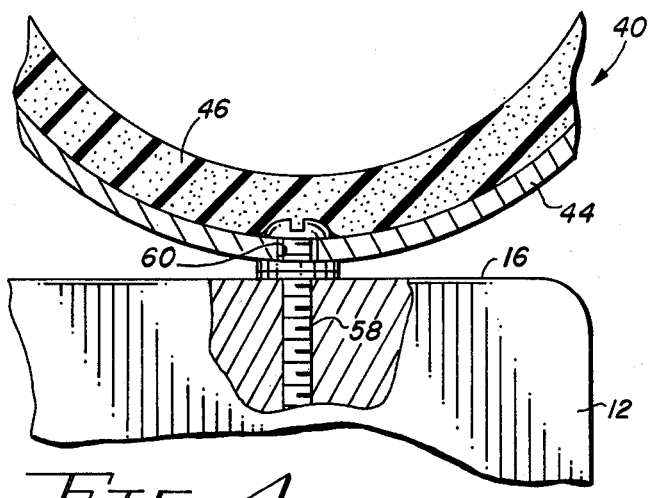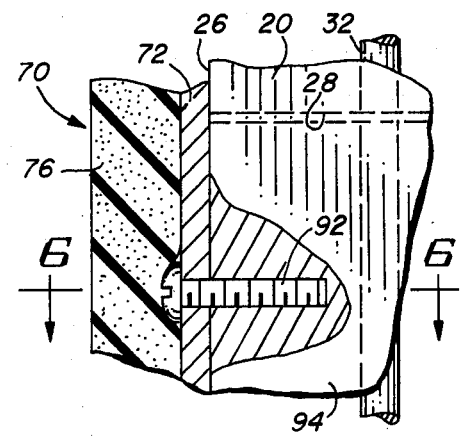

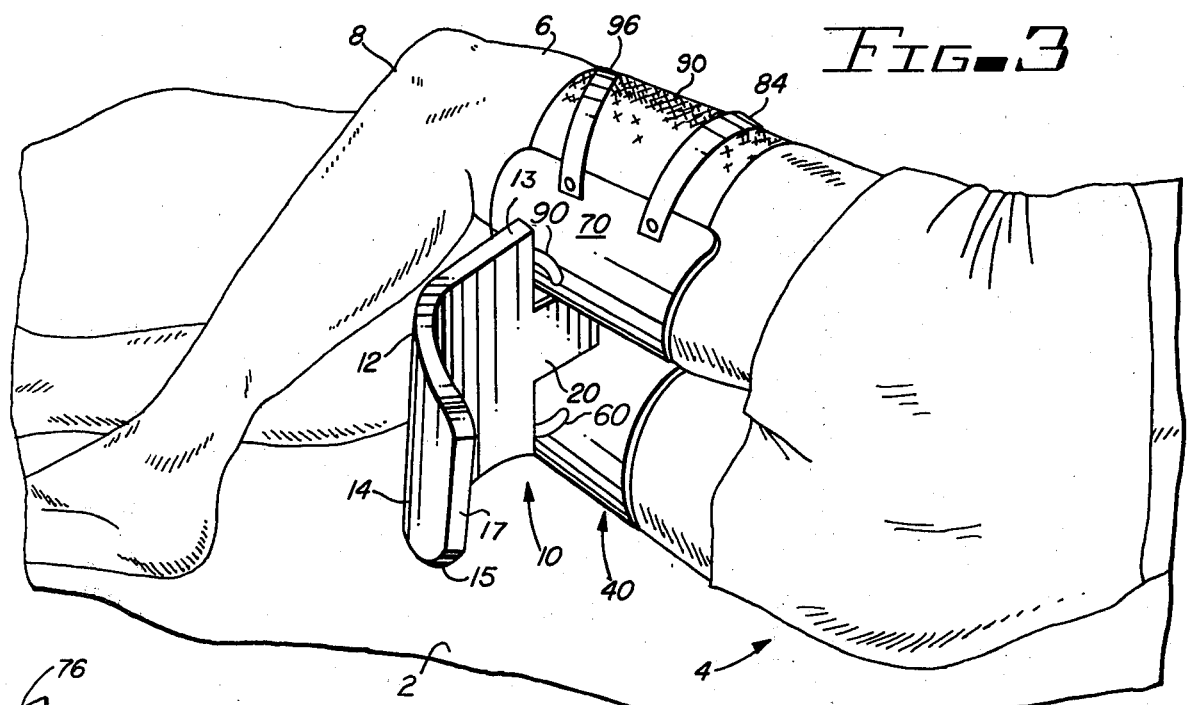
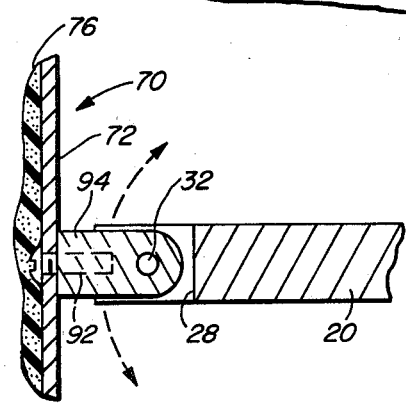
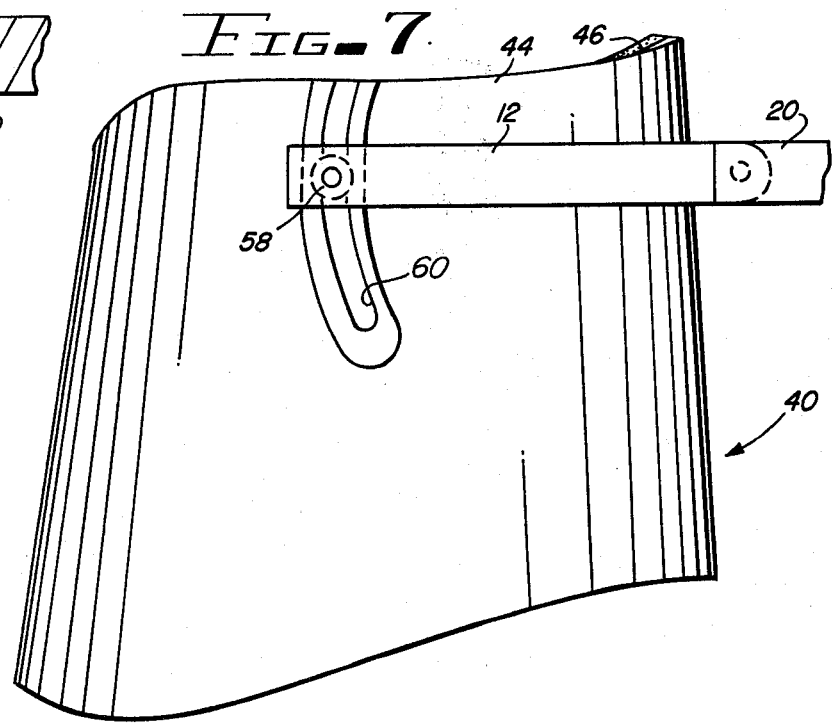

THIGH SUPPORT BRACE

BACKGROUND OF THE INVENTION

1. Field of the Invention

This invention relates to braces and, more particularly, to braces for supporting the thighs and separating the legs of the user for sleeping purposes when the user has a lower back injury or lower back and mid-back muscle tension and pain.

2. Description of the Prior Art

For persons with muscular strain or injury to the muscles of the lower back, sleeping and associated movement may be a relatively painful experience. The natural position of the thighs and legs, extending in line with the torso, is an inherently awkward position because there is a strain on the back muscles in that position. While sleeping on either side, the legs come together, and again there is strain and tension placed on the lower back muscles. The typical solution is to elevate the knees by placing a pillow under the thighs or knees, for sleeping on the back, or by placing a pillow between the legs for sleeping on either side. These are usually not satisfactory solutions because a pillow inevitably collapses or gets lost as a person turns or moves while sleeping.

The apparatus of the present invention immobilizes the thighs in an elevated position while a user is recumbent on his back, and accordingly relieves the lower back muscles of the muscular strain while in bed. The brace does not prevent the user from moving in a bed, such as moving from the user's back to either side. While sleeping on one's back, the knees are elevated and while sleeping on either side, one leg is elevated. In both positions, the strain on the muscles is relieved.

There have been different types of leg or brace supports in the prior art, but none of them have been devoted to supporting the thighs of a user to relieve lower back muscle strain. Accordingly, none of the thigh supports of the prior art accomplishes the task in the manner or for the same purpose as does the apparatus of the present invention.

U.S. Pat. No. 449,436 discloses apparatus for supporting and immobilizing a leg for examination or for surgical purposes. Such support includes a rest for the thigh secured to a base. However, the base is impractical for purposes of the present invention.

U.S. Pat. No. 2,910,707 discloses a pair of support elements, securable together to provide a bag for carrying such things as beach towels, etc. When separated, the elements provide a support for the head and shoulders and for the thighs and knees. Each support comprises a curved section, adapted to be placed on a relatively level surface. No provisions are included for securing the thighs to a support.

U.S. Pat. No. 2,926,977 discloses apparatus for holding the body in a particular position for inserting a bladder catheter. The apparatus includes individually adjustable knee supports secured to a relatively flat base on which a patient is placed. A strap secures the base to the lower abdomen of the patient, immobilizing the patient's hips, and movable supports are disposed beneath the knees of the patient and are appropriately secured to the patient. The knee supports are movable or adjustable to allow the apparatus to be used with patients of different sizes.

U.S. Pat. No. 2,978,713 discloses another type of apparatus for supporting legs. The apparatus includes a base with a pair of knee supports secured to the base. The base is adjustable with respect to its width to vary the distance between the knee supports and accordingly the knees. The knee supports are adjustable vertically to raise or lower the knees. The knee supports are also pivotable to vary the angular orientation between a user's thighs.

U.S. Pat. No. 3,104,446 discloses apparatus for positioning feet. It includes a pair of base elements secured to a fixed support element which includes a pair of "V" shaped support portions.

U.S. Pat. No. 3,145,397 discloses leg support apparatus which includes a trough which receives a leg and which is pivotally disposed on an arcuate support element. The purpose of the apparatus of the '397 patent is to allow a person with an immobilized leg to move that leg to different, perhaps more comfortable, positions.

U.S. Pat. No. 3,532,336 discloses body positioning apparatus which has a pair of fixed thigh and knee supports secured to a seat portion which accommodates the hips and buttocks of a person. The leg rests are disposed at a predetermined angular orientation away from each other so as to spread apart the thighs of the person using the apparatus. The purpose of the '336 apparatus is to provide a rest for a patient undergoing a pelvic or rectal examination by a physician.

U.S. Pat. No. 3,817,512 discloses apparatus for positioning the legs and thighs of a patient for pelvic or rectal examination, when the patient is confined to a bed. The apparatus includes a base support disposed on the bed, and a pair of leg supports extending upwardly from the base support. The leg supports may be oriented or adjusted as desired.

The apparatus of the patents described in the preceding paragraphs provide a common function of supporting the legs of the user, but each is designed for a specific purpose. None of the apparatus discussed above is usable or practical to be secured to a patient for sleeping purposes or for lying in bed to rest the lower back muscles. The apparatus of the above-discussed patents are not designed to, and accordingly will not, allow a patient to move from a recumbent position on the back to a side position. Moreover, none of the apparatus will allow a patient to move off of or out of a bed while the apparatus is still secured to the patient.

The apparatus of the present invention is designed to be secured to the thighs of a user and to immobilize a user's thighs with respect to each other to provide support for a user while in bed. This allows the muscular strain otherwise associated with lower back muscles to be relieved while the user is secured to the support apparatus. The support apparatus also allows the user to move off of a bed without having to remove the apparatus for necessary trips to the bathroom, etc.

SUMMARY OF THE INVENTION

The invention described and claimed herein comprises a base plate with a curved lower portion adapted to be disposed on a bed and with thigh supports which include straps for securing the apparatus to a user, and are secured to the base.

Among the objects of the present invention are the following:

to provide new and useful support apparatus;

to provide new and useful apparatus for supporting a user's knees in an elevated position on a bed;

to provide new and useful apparatus for separating a user's legs while the user is lying on a side;

to provide new and useful support apparatus for relieving the strain of the lower back muscles;

to provide new and useful support apparatus securable to a user which will allow a user to move or change positions in bed;

to provide new and useful apparatus for supporting a user's thighs on a bed; and to provide new and useful support apparatus securable to a user's thighs which is adjustable to the angular orientation of the user's thighs.

BRIEF DESCRIPTION OF THE DRAWING

FIG. 1 is a side view of the apparatus of the present invention showing the apparatus secured to the thighs of a recumbent user.

FIG. 2 is a front elevational view of the apparatus of FIG. 1, taken generally along line 2—2 of FIG. 1.

FIG. 3 is a perspective view of the apparatus of the present invention showing a user disposed on his side.

FIG. 4 is an enlarged view in partial section taken generally from circle 4 of FIG. 2.

FIG. 5 is an enlarged view in partial section of the apparatus of the present invention taken generally from circle 5 of FIG. 2.

FIG. 6 is an enlarged view in partial section of a portion of the apparatus of the present invention taken generally along line 6—6 of FIG. 5.

FIG. 7 is an enlarged bottom view of a portion of the apparatus of the present invention.

DESCRIPTION OF THE PREFERRED EMBODIMENT

FIG. 1 comprises a side view of a portion of a human body lying down on its back with support brace apparatus 10 of the present invention secured to the thighs. FIG. 2 is a front view of the support brace apparatus 10 of FIG. 1. FIG. 3 is a view of the apparatus 10 secured to a user, with the user disposed on his side. FIG. 4 is an enlarged view in partial section of a portion of the support brace apparatus 10 of FIG. 2, taken generally from circle 4 of FIG. 2. FIG. 5 is an enlarged view in partial section of a portion of the support brace apparatus 10, taken generally from circle 5 of FIG. 2. FIG. 6 is a view in partial section of a portion of the apparatus 10, taken generally along line 6—6 of FIG. 5. FIG. 7 is a view in partial section of a portion of the apparatus 10, taken generally along line 7—7 of FIG. 2. FIG. 8 is a bottom view of a portion of the apparatus 10, illustrating the angular adjustment of a thigh support. FIGS. 4 through 9 illustrate details of the support brace apparatus 10. For the following discussion of the support brace apparatus 10, reference will be made to FIGS. 1 through 9.

The support brace 10 includes a plate 12 which comprises the base of the apparatus. The base or plate 12 includes a curved bottom portion 14 which extends generally downwardly and rearwardly, or toward the torso of the user, as best shown in FIGS. 1 and 3. Secured or attached in an adjustable manner to the plate or base 12 is a pair of thigh supports 40 and 70. The thighs of the user are appropriately secured to the thigh supports 40 and 70, as by straps, to secure the support brace apparatus 10 to the user.

As shown in FIG. 1, an individual user is shown in a reclining or recumbent (supine) position, disposed on a surface 2, which may be a bed, or the like. The body of the user illustrated in FIG. 1 includes a torso 4 and a thigh 6, which is a right thigh. A knee 8, which is the right knee, is also illustrated in FIG. 1. The apparatus 10 is secured to the thighs of the user, intermediate the user's torso 4 and his knees. The plate 12 extends downwardly from the thigh supports, generally perpendicularly to the longitudinal axis of the thigh supports, and accordingly perpendicularly to the longitudinal axis of the user's thighs. The curved bottom portion 14 extends downwardly and rearwardly from the lower portion of the plate 12. The curved portion extends in the direction of the torso 4 and away from the knee 8. The curved portion 14 helps to provide stability and support for the apparatus. If the base plate omitted the curved lower portion 14, the tendency would be for the plate to wobble or to pull the legs downwardly. The curved portion 14 also helps to hold the legs up for proper support of the legs, which in turn allows the back muscles to rest. If the apparatus were to allow the legs to move downwardly, there might result a substantial strain not only on the user's back muscles, but also on the connection of the thigh supports 40 and 70 and the plate 12, which will be discussed in detail below in conjunction with FIG. 4.

It will be noted from FIG. 2 that the width of the plate 12, including its curved bottom portion 14, is less than the overall width of the thigh supports 40 and 70, from the outside of the thigh support to the outside of the other thigh support. Accordingly, when the user is disposed or reclining on one or the other side, such as shown in FIG. 3, the plate 12 does not interfere with the legs resting on the bed or other surface on which the user is disposed. The curved bottom 14 includes curved side edges or radiused corners 15 which extend from side edges 13 of the plate 12 to a generally flat or planar bottom edge 17.

The plate or base 12 includes a pair of spaced apart but aligned upper edges 16 and 18, separated by a center plate portion 20 which extends upwardly between the edges 16 and 18. The center plate portion 20 includes a pair of side edges 22 and 26, which are substantially perpendicular to the adjacent edges 16 and 18, respectively, of the base plate 12. The center plate portion 20 is disposed between and is connected to the thigh supports 40 and 70, and spaces them apart.

The center plate 20 includes a pair of relieved portions 24 and 28 which extend inwardly from the sides 22 and 26 respectively. The relieved portions receive hinge plates secured to the thigh supports 40 and 70. This will be discussed in detail below in conjunction with FIGS. 5 and 6.

The thigh support 40, which receives the right thigh of a user, includes a side portion 42 connected to a bottom trough portion 44. A pad or lining 46 is disposed within the thigh support as a cushion for the leg. The user's thigh 6 is secured to the thigh support 40 by a pair of straps. A portion of each pair of straps is secured to the outer portion of the bottom trough 44 and the upper portion of the side 42. In FIG. 2, a strap portion 48 is shown secured to the upper portion of the side 42 by a rivet 52. The strap 48 includes a buckle 50 remote from the rivet 52. A strap portion 54 is secured by a rivet 56 to the outer portion of the bottom trough 44, remote from the side 42. The buckle 50 receives the free end of the strap 54, remote from the rivet 56. If desired, fastening means other than the rivets 52 and 56 may be used to secure the straps to the thigh supports. Moreover, "Velcro" fasteners, or some other type of fasteners, may be used rather than buckles for securing the straps together, and the user to the thigh supports and the apparatus 10.

In addition to the strap portion 54, which mates with the strap portion 48, FIG. 1 shows a second strap portion 66 also secured to the thigh support 40. The strap 66 is in an axially spaced apart orientation with respect to the strap 54. The pair of straps 54 and 66 are accordingly used to secure the thigh 6 to the thigh support 40. It is preferable that two straps, spaced apart from each other axially with respect to the thigh supports, be used rather than a single strap. The two straps 54 and 66 insure that the user is securely fastened to the thigh supports 40 and accordingly to the apparatus 10.

Within the relieved portion 24, which extends inwardly from the side 22 of the center plate portion 20, there is disposed a hinge plate 64. The hinge plate 64 is appropriately secured to the side portion 42 of the thigh support 40 by a pin 30. The pin 30 extends downwardly through the center plate 20 and through the hinge plate 64. The hinge plate 64 and the thigh support 40 secured to it accordingly pivot on the pin 30.

The thigh support 70 is substantially identical to the thigh support 40. The thigh support 70 includes a side portion 72 and a bottom trough portion 74. Appropriate foam or other liner 76 is disposed inside the thigh support 70 and comprises appropriate padding for the left thigh (see FIG. 3) of the user of the apparatus. A pair of straps are used to secure the user's left thigh to the thigh support 70. In FIG. 2 is shown one of the straps, including a strap portion 78 which is secured to the side portion 72 by a rivet 82, and a strap portion 84 which is secured to the bottom trough portion 74 by a rivet 86. The strap 78 includes a buckle 80, remote from the rivet 82. The buckle 80 receives one end of the strap 84, namely the free end, remote from the rivet 86. The straps 78 and 84 are used, as are the straps 48 and 54, to secure a thigh, namely the left thigh, of a user to the support brace apparatus 10. A second pair of straps, including a strap portion 96, shown in FIG. 3, is also used to secure the user to the thigh support 70.

A hinge plate 94 is disposed within the relieved portion 28 of the center plate 20. The hinge plate 94 is appropriately secured to the thigh support 70, as will be discussed below in conjunction with FIG. 5. The thigh support 70 and the hinge plate 94 pivot on a pin 32 which extends through the hinge plate 94 and into the center plate 20. Both thigh supports 40 and 70 move in a pivoting manner on their respective hinge plates 64 and 94, with respect to the plate 20 and to the base 12.

As the thigh supports 40 and 70 move, there is a corresponding arcuate movement of the lower or trough portions 44 and 74, respectively, of the thigh supports with respect to the edges 16 and 18 of the base 12. The movement is illustrated in FIGS. 4 and 7. FIG. 4 comprises an enlarged view in partial section of the lower, trough portion 44 of the thigh support 40 and of the upper portion of the base 12, at the edge 16. FIG. 7 is a bottom view of the thigh support 40.

The thigh support 40 includes an arcuately extending slot 60 at the lower portion of the trough 44, through which the head of a screw 58 extends. The screw 58 extends into the base 12, where it is appropriately secured. For adjusting the angle of the thigh support 50 with respect to the base 12 and to the center plate 20, the screw 58 is appropriately loosened to allow it to move relatively freely in the slot 60 as the orientation of the thigh support 40 is adjusted. When the proper angular orientation of the thigh support 40 has been accomplished, the screw 58 is tightened to hold the thigh support 40 securely with respect to the base 12 and the center plate 20. A similar pivoting relationship exists between the thigh support 70 and the base 12, at its upper edge 18 and the center plate 20. An appropriate screw mechanism or assembly 88 is shown in FIG. 2, comparable to the screw 58 with its washer, etc. A slot 90 is shown in FIG. 3. The screw assembly 88 of FIG. 2 is associated with the slot 90 substantially as discussed above with respect to the slot 60 and its screw 58 and associated washer.

For securing the thigh supports to their respective hinge plates, a screw, such as the screw 92 shown in FIG. 5, is used. The screw 92 is shown extending through an appropriate aperture in the side portion 72 of the thigh support 70 and into the hinge 94. It will be noted that the screw 92 is secured in a fixed manner with respect to the side 72 of the trough 70 and to the hinge plate 94, and they accordingly move as a unit. The hinge plate 94 and the thigh support 70 pivot as a unit on the pivot pin 32.

An arcuate slot (not shown) extends through the bottom portion 74 of the thigh support 70 to allow the thigh support 70 to move relative to the base 12. The operation of the screw assembly 88 with respect to the thigh support 70 is substantially the same as has been described above, with respect to the thigh support 40 and the base 12, and as illustrated in FIG. 4.

FIG. 6, which is a view in partial section taken generally along line 6—6 of FIG. 5, comprises a top view through the hinge plate 94 and its pivot pin 32. The hinge plate 94 is secured to the thigh rest 70 by the screw 92. The screw 92 fastens the thigh rest 70, through the side 72, securely and fixedly to the hinge plate 94. The hinge plate 94 is in turn secured to the upper plate portion 20 on the pin 32 which extends through the plate 94 and through the relieved portion 28 into the plate portion 20. The pin 32 extends into the plate portion 20 on both sides of the relieved portion 28, both "top" and "bottom" as viewed in FIG. 2. The pivot pin is inserted from the top through the relieved portion 28 and the hinge plate 94, and into an appropriately drilled aperture within the plate portion 20. The pin 32 is accordingly appropriately supported by the center plate portion 20. The plate 94 pivots on the plate 32 in response to movement of the thigh support 70.

As discussed above, the screw 88, disposed at the bottom of the trough 74, extends through the bottom of the trough and into the base 12 in order to allow the thigh support 70 to pivot relative to the base 12 and to the center plate 20. Once the thigh support has been moved to its desirable position, the screw 88 is then tightened to lock the thigh support 70 in place with respect to the base 12 and also with respect to the center plate 20. The hinge plate 94 accordingly is more of an anchor plate for securing the side of the thigh support 70 to the center plate 20 than it is a freely movable hinge. The movement of the hinge is limited, as desired, by the user of the apparatus.

The above remarks regarding the thigh support 70 and its hinge plate 94, and the relative movement of the thigh support 70 with respect to the base 12 and to the center plate 20 is also applicable to the thigh support 40 and to its hinge plate 64. Moreover, the comments with respect to the pivot pin 32, the hinge plate 94, and the center plate 20 are also applicable to the pivot pin 30 and to the hinge plate 64. The movement of the thigh support 40 is substantially the same as discussed with respect to the thigh support 70.

FIG. 1 shows a user lying on his back, with the bottom edge 17 of the base plate 12 disposed against the surface 2 of a bed, or the like. FIG. 5 shows the user disposed on his right side, with his thighs maintained in a fixed, spread-apart position relative to each other, since both thighs are secured in the respective thigh supports 40 and 70 of the support brace apparatus 10. The base plate 12 is disposed on the surface 2 on one of its side edges 13. The curvature of the lower side edge 15 enhances the ability of the user to turn from the recumbent position shown in FIG. 1 to the position shown in FIG. 3. The turning movement, which is actually a rolling movement, of the user is accomplished with minimum discomfort or problems because at all times the thighs are maintained in their fixed, spaced-apart relation with respect to each other regardless of the position of the user or of the user's torso. The support apparatus 10 accordingly provides the necessary support for the user and relieves the strain of the lower back muscles, which strain would otherwise be present.

With the support brace apparatus 10, the rolling movement of the user from the position shown in FIG. 3 to the position shown in FIG. 1, and/or to a rolling movement on the user's other side from that shown in FIG. 3, is also simplified and enhanced by a brace support apparatus 10 and its curved side edges. The maintenance of the thighs in their fixed, spaced apart relationship is assured, regardless of the rolling or angular movement of the torso and legs of the user, to relieve the back musclles of any strain during such movements.

For adjusting the angle of the thighs and the thigh supports, with respect to the torso, laterally, as been discussed above in conjunction with the pivoting or angular adjustment of the thigh supports 40 and 70. For adjusting the orientation of the thighs vertically with respect to the longitudinal axis of the user's torso, the brace support apparatus 10 is moved longitudinally along the thighs. This may best be understood with reference to FIG. 1. For example, if it is desired by the user to lower the elevation of his knees and thighs with respect to the surface 2, the support brace apparatus 10 is moved away from the torso 4, or downwardly along the thigh(s) 6 and closer to the knee(s) 8. This movement of the brace apparatus 10 lowers the angular orientation between the surface 2 and the thigh(s) 6. A reverse movement of the support brace apparatus 10 along the thigh(s), or moving the apparatus longitudinally along the thighs toward the torso and away from the knees, results in raising the user's thighs, thus increasing the angle between the surface 2 on which the user is disposed and the user's thighs.

In addition to the padding 46 and 76 illustrated in the drawing and within the thigh supports 40 and 70, respectively, additional wrapping or padding, such as elastic cloth 68 and 90, may be inserted or used within the thigh supports, as shown in FIGS. 1 and 3, respectively. The elastic cloth 68 is shown as being disposed underneath the straps 54 and 66. The particular type of wrap or pad used with the thigh supports may vary in accordance with the desires, comfort, etc., of the user. Typically, the elastic cloth, using appropriate fasteners such as "Velcro" fasteners, may be used to secure the elastic cloth to the user's thighs. For purposes of clarity, the elastic cloth is shown only in FIGS. 1 and 3 and is not shown in FIGS. 2, 4, or 5.

The elastic cloth 68 and 90 may be appropriately secured to the thigh supports 40 and 70, respectively, as by rivets (not shown). When secured to the thigh supports and to the user's thighs, the elastic cloth becomes the primary means of securing the support apparatus 10 to a user. The straps then become a secondary fastening means. With the elastic cloth covering a relatively large area of a user's thighs, as compared to the area covered by the straps, the elastic cloth comprises a more comfortable and more practical way to secure the apparatus to a user.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted for specific environments and operative requirements without departing from those principles. The appended claims are intended to cover and embrace any and all such modifications, within the limits only of the true spirit and scope of the invention. This specification and the appended claims have been prepared in accordance with the application patent laws and the rules promulgated under the authority thereof.

What is claimed is:

1. Support brace apparatus for supporting the thighs of a user, comprising, in combination:
   base plate means, including
      a bottom plate portion having a portion thereof curved toward the user's torso, and
      a center plate portion remote from the curved bottom portion extending from said bottom plate portion;
   thigh support means pivotally attached to the base plate means, including
      a first thigh support,
      an arcuately extending first slot in the first thigh support,
      means extending through the arcuately extending first slot for securing the first thigh support to the bottom plate portion,
      a second thigh support,
      an arcuately extending second slot in the second thigh support, and
      means extending through the arcuately extending second slot for securing the second thigh support to the center plate portion;
   a first hinge secured to the first thigh support and pivotally secured to the center plate;
   a second high secured to the second thigh support and pivotally secured to the center plate in juxtaposed relation to said first hinge; and
   means for securing the thigh support means to the thighs of a user to secure the user to the support brace apparatus.

2. The apparatus of claim 1 in which the means for securing the thigh support means to the thighs of a user comprises straps secured to the thigh support means and adapted to extend about the user's thighs when the user's thighs are disposed in the thigh support means.

3. The apparatus of claim 1 in which the curved portion of the bottom plate portion includes side edges and a flat bottom edge and radiused corners extending to the flat bottom edge from the side edges for enhancing a rolling movement of the user between various body positions.

4. The apparatus of claim 1 wherein the bottom plate portion is wider than the center plate portion.

* * * * *